United States Patent [19]

Boltong

[11] Patent Number: 5,605,713
[45] Date of Patent: Feb. 25, 1997

[54] PROCESS FOR THE PREPARATION OF CALCIUM PHOSPHATE CEMENTS AND ITS APPLICATION AS BIO-MATERIALS

[76] Inventor: Maria G. Boltong, Menzenlaan 12, NL-6581 CM Malden, Netherlands

[21] Appl. No.: 389,624

[22] Filed: Feb. 15, 1995

Related U.S. Application Data

[63] Continuation-in-part of Ser. No. 970,028, Nov. 2, 1992, abandoned.

[30] Foreign Application Priority Data

Nov. 22, 1991 [ES] Spain ..................... 9102606

[51] Int. Cl.$^6$ ............... A61C 13/00; A61L 27/00; C04B 12/02
[52] U.S. Cl. ............... 427/2.1; 106/35; 106/690; 106/691; 427/2.29; 433/228.1; 606/76
[58] Field of Search ............... 106/35, 690, 691; 427/372.2, 2.29, 2.1; 433/228.1; 501/1; 606/76; 623/16

[56] References Cited

U.S. PATENT DOCUMENTS

| | | | |
|---|---|---|---|
| 4,518,430 | 5/1985 | Brown et al. | 106/35 |
| 4,612,053 | 9/1986 | Brown et al. | 106/35 |
| 4,673,355 | 6/1987 | Farris et al. | 106/35 |
| 5,129,905 | 7/1992 | Constantz | 106/35 |
| 5,152,836 | 10/1992 | Hirano et al. | 106/35 |

FOREIGN PATENT DOCUMENTS

| | | | |
|---|---|---|---|
| 59-182263 | 10/1984 | Japan | 106/35 |

OTHER PUBLICATIONS

SIGMA Chemicals Catalog, "Transforming Growth Factor β (TGF–β)", p. 1274, (no date).

Y. Fukase, E. D. Eanes, S. Takagi, L. C. Chow, and W. E. Brown, Setting Reactions and Compressive Strengths of Calcium Phosphate Cements, J. Dent. Res. 69 1852–1956 (1990) no month.

A. Mirtchi, J. Lemaitre and E. Munting, Calcium Phosphate Cements: action of setting regulators on the properties of the β–tricalcium–phosphate–monocalcium phosphate system, Bio–materials 10 634–638 (1989) no month.

M. Ito, In Vitro Properties of A Chitosan–bonded Hydroxyapatite Bone–Filling Paste, Bio–materials 12 41–45 (1991).

H. Oonishi, Orthopaedic applications of hydroxyapatite, Bio–materials 12 171–178 (1991) no month.

H. Monma, A Makishima, M. Mitomo and T. Ikegami, Hydraulic Properties of the Tricalcium Phosphate–dicalcium Phosphate Mixture, Nippon–Seramikkusu–Kyokai–Gakujutsu–Ronbushi, 96 878–809 (1988) no month.

J. Lemaitre, A. Mirtchi and A. Mortier, Calcium Phosphate Cements for Medical Use; state of the art and perspectives of development, Sil. Ind. Ceram. Sci. Technol. 52 141–146 (1987) no month.

H. Monma and T. Kanazawa, The hydration of α–Tricalcium phosphate, Yogio–Kyokai–Shi 84 209–213 (1976) no month.

H. Monma, Hydration and Hardening of Brushite and Monetite, Yogio–Kyokai–Shi 95 284–285 (1987) no month.

F. C. M Driessens and R. M. H. Verbeeck, Relation Between Physico–chemical Solubility and Biodegradability of Calcium Phosphates, in: C de Putter, G. L. de Lange, K. de Groot and A. J. C. Lee (Eds.), Implant materials in biofunction Elsevier, Amsterdam, 1988, no month pp. 105–111.

F. C. M. Driessens, Is the solubility product of synthetic calcium phosphates a good predictor of their biodegradbility?, In: G de With, R. A. Terpstra and R. Metselaar (Eds.), Euroceramics, Elsevier, London, 1989 no month, pp. 3.48–3.52.

M. M. A. Ramselaar, F. C. M. Driessens, W. Kalk, J. R. de Wijn and P. J. van Mullem, Biodegradation of four calcium phosphate ceramics: in vivo rates and tissues interactions. J. NeutlSci., Mat'l in Med. 2, 63–70 (1991) no month.

N. Nishimura, T. Yansamuro, T. Yakamura, Y. Taguchi, T. Kokubo and S. Yoshihara, A novel bioactive bone cement based on CaO–SiO$_2$–P$_2$O$_5$–CaF$_2$ glass, in: W. Bonfield, G. W. Hastings and K. E. Tanner (Eds.) Bioceramics, vol. 4, Butterworth–Heinemann, London, 1991 no month, pp. 295–299.

H. Oonish; Orthopaedic applications of Hydroxyapatite, Biomaterials v. 12 171–178 (1991) no month.

F. C. M. Driessens, Physiology of Hard Tissues in Comparison with the Solubility of Synthetic Calcium Phosphate, Annals of the New York Academy of Sciences, 523 131–136 (1988) no month.

A. Mirtchi, J. Lemaitre, N. Terao, Calcium phosphate cements: study of the β–tricalcium phosphate—mono calcium phosphate system, Biomaterials 1989 no month, vol. 10 475–480.

*Primary Examiner*—Anthony Green
*Attorney, Agent, or Firm*—Fitzpatrick, Cella, Harper & Scinto

[57] ABSTRACT

The invention refers to the use of a series of calcium orthophosphate cements as bio-materials, starting from a number of components by grinding and sieving to obtain the adequate grain size, the needed quantity being weighed and the blend of powder products being put into recipients to be shaken up for its homogenization, the mix being placed afterwards, in the desired portions, into a container to be supplied to the specialists, together with capsules containing water or a water solution.

9 Claims, No Drawings

PROCESS FOR THE PREPARATION OF CALCIUM PHOSPHATE CEMENTS AND ITS APPLICATION AS BIO-MATERIALS

This application is a continuation-in-part of application Ser. No. 07/970,028 filed Nov. 2, 1992 now abandoned.

BACKGROUND OF THE INVENTION

1. Subject of the Invention

The present invention refers to a process for the preparation of calcium phosphate cements and their application as bio-materials, which obvious objective is to allow their use in bone surgery and odontology.

2. Field of the Invention

This invention corresponds to the field of the industrial manufacture of bio-materials for bone surgery and odontology.

3. Description of Prior Art

Calcium and orthophosphate ions are regularly contained in body fluids and in the mineral substance forming parts of bones, dentine and dental enamel.

These are calcium orthophosphates, which additionally contain sodium, magnesium and carbonates. Sintered hydroxyapatite and calcium tri-phosphate, as well as other synthetic calcium orthophosphates, implanted in a number of test animals, as well as human beings, have been shown to be bio-compatible.

It has been observed from the use of these kinds of materials that they are bone growth promoters, that is, after implantation in bone tissue they promote their own growth.

A negative aspect of calcium sintered orthophosphates for use in surgery is that they have to be molded prior to the intervention, while orthophosphate cements do not show this disadvantage, because of their cement nature which allows them to be molded by the surgeon during the intervention.

At present the existence of solids corresponding to the system $Ca(OH)_2$—$H_3PO_4$—$H_2O$ at room or physiologic temperature is already known. Cement formulations are also known for the calcium orthophosphate system. Finally, other formulations are known from other inventions, for which reason they are excluded from the patent disclosure.

Concerning the solids belonging to the $Ca(OH)_2$—$H_3PO_4$—$H_2O$ system, a table is included in the following in which the solids which may be formed in this system at ambient or body temperature are described.

Given the fact that pH in bone in the vicinity of osteoclasts, osteoblasts and other osteocites may vary in a range between approximately 5 and 8, it has been observed that the final result of the solidification or setting reaction in a calcium orthophosphate cement will generally adopt the CDA form, which in physiological conditions will incorporate sodium and carbonate ions.

In bloodstream the apatites $Ca_{8.5}Na_{1.5}(PO_4)_{4.5}(CO_3)_{2.5}$ or NCCA and $Ca_9(PO_4)_{4.5}(CO_3)_{1.5}(OH)_{1.5}$ or HCDHA may be formed by precipitation.

Given the fact that magnesium ions may be present, the final result may consist in magnesium whitlockite or MWH.

PHA could also result by the action of some fluorides.

In each of the above cases, the intermediate formation of DCPD or OCP is also possible.

In case that in a formulation of calcium orthophosphate some solidification reaction appears, it will be due to the framework constituted with the recently formed crystals.

As consequence, the best results which can be expected from a calcium orthophosphate cement, as concerns mechanical properties, consist in that this cement may come close to the mechanical characteristics of hard dental gypsum or other hard gypsum formations in which the framework of similar crystals (dicalcium sulphate dihydrate) is the mechanism for solidification or setting.

The solids appearing in the system $Ca(OH)_2$—$H_3PO_4$—$H_2O$ at ambient temperature or physiological temperature (1) are those shown in following table 1:

TABLE 1

| Abbreviation | Ca/P | Formula | Formation conditions and relative stability |
|---|---|---|---|
| MCPM | 0.5 | $Ca(H_2PO_4)_2.H_2O$ | Established below pH 2 approximately. |
| Brushite or DCPD | 1.0 | $CaHPO_4.2H_2O$ | Established at pH between 2 and 4, rapid nucleation and growth up to pH > 6.5. |
| OCP | 1.33 | $Ca_8(HPO_4)_2(PO_4)_4.5H_2O$ | Rapid nucleation and growth in pH 6.5 to 8, more stable than DCPD or ACP in the same range. |
| ACP | 1.5 | $Ca_3(PO_4)_2.H_2O$ | This substance appears as a first stage when the precipitation takes place at high concentrations with pH between 4 and 8, however it spontaneously transforms into DCPD, OCP or CDA. By any means, by the incorporation of magnesium ions it will transform into magnesium whitlockite NWH is as stable as CDA. |
| CDA | 1.5 | $Ca_9(HPO_4)(PO_4)_5OH$ | This calcium poor apatite does not spontaneously precipitate, however it has DCPD or OCP as precursors. By any means, it may rest indefinitely in metastable balance with aqueous solution. |
| PHA | 1.67 | $Ca_{10}(PO_4)_6(OH)_2$ | The precipitated hydroxyapatite is the most stable calcium orthophosphate. It only precipitates above pH 8. By any means, its nucleation with low pH maybe started by fluoride ions. |
| — | $\infty$ | $Ca(OH)_2$ | This solid is stable only with a high pH in absence of orthophosphates. |

Concerning cement formulations for the calcium orthophosphate system, any water based or water solution based cement as intermediate fluid medium, contains the following components:

a) An acidic component which may emit $H^+$ ions which may be converted into a solid salt by reaction with dissolved ions.

b) A basic component which by reaction with the emitted $H^+$ ions may be able to emit the dissolved cations and, by this reaction, will become a more or less stable and neutral gel or solid acid. It is also possible that the acidic component and the basic component react together forming one solid component.

c) Water or a water solution in which both the acidic and the basic components may dissolve working as a reaction medium.

d) Eventually, accelerators, inhibitors or modifiers.

For the formulation of calcium orthophosphate cements the choice is not limited to the solids appearing in the foregoing table.

Other solids may be incorporated into similar calcium containing components, specially those formed at high temperatures.

In the following Table 2 some relevant solids which may be prepared at a high temperature are shown.

calcium orthophosphate cements, it will be possible to use water solutions containing phosphoric, malonic, lactic, citric or other organic acids which are present in body fluids.

Given the fact that both the body fluids and the minerals are contained in bones which also comprise sodium carbonates, magnesium, sulphates, hydrochloric and hydroflouric acid, other components, particularly those mentioned in the following Table 3 may be also considered to fall within the calcium orthophosphate cement formulations.

In Table 3 a relation of solids will be shown which is relevant for the formulation of calcium orthophosphate cements, possibly appropriate as accelerators, inhibitors or even as substitute reagents for the acidic or basic components or as reaction products for the reagents which constitute a cement.

TABLE 2

| Abbreviation | Ca/P | Formula | Formation conditions and relative stability in water at ambient or physiological temperature |
|---|---|---|---|
| DCP or monetite | 1.0 | $CaHPO_4$ | Formed by precipitation at high temperature, it is somewhat more stable than DCPD. |
| β-TCP | 1.5 | $Ca_3(PO_4)_2$ | Formed by heating to temperature up to 1,189° C. More stable than DCPD and OCP but less stable than CDA in the 6 to 8 pH range. |
| α-TCP | 1.5 | $Ca_3(PO_4)_2$ | Formed by heating to over 1,180° C. and rapid cooling. It is less stable than DCPD or OCP. |
| SHA | 1.67 | $Ca_{10}(PO_4)_6(OH)_{2-2x}O_x$ | Sintered hydroxyapatite. It is formed by heating in the 700 to 1,440° C. range. It is as stable as CDA. |
| TTCP | 2.0 | $Ca_4(PO_4)_2O$ | Formed by heating starting from 1,500° C. It is less stable than SHA, CDA, DCPD, and OCP in slightly acidic medium. After 450° C. it is less stable than $Ca(OH)_2$ and therefore it is to be expected to be more reactive. |
| — | ∞ | CaO | Formed by heating $CaCo_3$ beginning at 450° C. |

Additionally, to accelerate or to control the time necessary for setting or to improve the mechanical properties of

TABLE 3

| Compounds which contain | Formulae |
|---|---|
| Sodium | * $CaNaPO_4$(α or β form), $Ca_{10}Na(PO_4)_7$(α or β form) $Ca_{8.5}Na_{1.5}(PO_4)_{4.5}(CO_3)_{2.5}$<br>* NaF<br>* $Na_2CO_3$, $Na_2SO_4$, NaCl, Na orthophosphates |
| Potassium | * $CAKPO_4$, $Ca_9K(PO_4)_5(CO_3)_2$<br>* KF<br>* $K_2CO_3$, $K_2SO_4$, KCl, K orthophosphates |
| Magnesium | * $Ca_4Mg_5(PO_4)_3$, $MgHPO_4$, $Mg_3(PO_4)_2 \cdot 4H_2O$<br>* $MgF_2$<br>* $MgCo_3$, $CaMg(CO_3)_2$, $MgSO_4$, $MgCl_2$, MgO, $Mg(OH)_2$ |
| Zinc | * $CaZn_2(PO_4)_2$, $Zn_3(PO_4)_2 \cdot 4H_2O$<br>* $ZnF_2$<br>* $ZnCO_3$, $ZnSO_4$, $ZnCl_2$, ZnO, $Zn(OH)_2$ |
| Calcium | * $CaSO_4$, $CaSO_4 \cdot 2H_2O$, $CaSO_4 \cdot \frac{1}{2}H_2O$ |

TABLE 3-continued

| Compounds which contain | Formulae |
|---|---|
| | * $CaF_2$, $Ca_{10}(PO_4)_6F_2$ |
| | * $CaCo_3$, $CaCl_2$, $Ca_2PO_4Cl$, $Ca_{10}(PO_4)_6Cl_2$ |
| Biopolymers | Proteins, peptides, proteoglycans, glucoseamoglycans, carbohydrates, etc. |
| Organic acids | Citric acid, malonic acid, pirmic acid, tartaric acid, etc. |
| Inorganic acids | Phosphoric acid, etc. |
| Synthetic polymers | Polylactic acid, polyglycolic acid, etc. |
| Growth factor | Transforming Growth Factor, T.G.F.-$\beta$, etc. |

Solid carbonates are less desirable because carbon dioxide which may form during the reaction may cause the structure to explode, that is, it may affect structure.

The only advantage that the carbonate may bring about is that as a consequence, a solid structure may be formed at the same time which is porous and, in which structure the bone marrow may show some degree of growth.

Hydrates are less desirable as reactive components when the setting reaction water may be formed, weakening the structure.

However, DFP or OCP as reaction products may be favorable because they bind with water so they may reduce the volume of the reaction products.

With the list of possibilities shown in Tables 1 and 2, we arrive at the following components which are deemed to be appropriate, shown in decreasing acidity or basicity:

a) Acidic components: MCPM>DCPD= DCP>OCP>ACP=$\beta$-TCP=$\alpha$-TCP=CDA.

b) Basic components: CaO=Ca(OH)$_2$>TTCP>PHA= SHA>$\alpha$-TCP=CDA=$\beta$-TCP=ACP.

The setting reaction may be accelerated and even induced by the addition of crystal seeds of CDPD, OCP, $\beta$-TCP, CDA, PHA or SHA.

Table 3 contains as well a list of other possibilities which are physiologically acceptable to initiate, accelerate or to delay the setting reaction.

Peptides and proteins as well as protoglycans may be used additionally as modifiers with the aim of obtaining a greater approximation to the composition of the bones.

Also composites with synthetic reabsorbable or non-reabsorbable synthetic polymers may be formed, being of importance the fact that growth factors like TGF-$\beta$ may be easily incorporated into these calcium phosphate based cements with the aim of stimulating the growth of the bone.

Among the formulations which have been previously disclosed and that are excluded from this invention, formulations based on TTCP as basic component in combination with other calcium phosphates may be cited.

U.S. Pat. No. 4,518,430 to Brown and Chow mentions as acidic components DCDP, DCP, OCP, $\alpha$-TCP and $\beta$-TCP.

The reaction with DCPC which takes approximately one week, may be accelerated by the addition of HA, a 48% addition causing the settling time to diminish from 22 to 8 minutes.

The combination of TTCP with, as shown in Fukase, was more successful.

By the addition of some fluoride to the blend to prevent its nucleation it was observed that the reaction product consisted in PHA.

In this last combination the inventors found that the reaction was completed in 24 hours.

Brown and Chow inventors determined a compression resistance of 37 MPa although Monma, Makishima, Mitomo and Ikegami indicate for the combination of TTCP with DCPD values comprised between and 11 MPa. The porosity is about 50% (4).

Concerning the combination of MCPM with $\beta$-TCP the inventors are Mirtschi, Lemaitre and collaborators observing for 2 minutes the setting in combinations with $\beta$-TCP.

The product of the reaction was DCPD and the tensile resistance varies between 0.2 and 1.1 MPa.

The tensile resistance was lowered by drying and aging in water.

The addition of calcium pyrophosphate, calcium sulphate, dihydrate or hemihydrate calcium sulphate increases the setting time up to approximately 10 minutes and the tensile resistance in dry state to about 3 MPa, by.

By any means, even in that case the resistance decreases with the aging in a saliva solution.

The combination of $\alpha$-TCP with DCPD is also known by Monma and his collaborators having studied the hydration of $\alpha$-tricalcic phosphate.

The reaction rate decreases with temperature and pH.

The final product was CDA and even at 60° C. the setting time was of some hours and the porosity was of 60%. The compression resistance was of about 17 MPa and the tensile resistance reached 3 MPa. This combination is not adequate as a cement due to its long setting time.

Monma also studied the hydration and hardening of brushite and monetite.

The hardening was obtained by the addition of CaCo$_3$ and water.

The final products were OCP and carbonate containing apatite.

The porosity was of approximately 75% and the tensile resistance in dry state varied within the 0.1 to 1.5 MPa range.

Due to the fact that the setting time was approximately 1 hour at a temperature between 50 and 80° C., this combination was not adequate for clinical purposes.

Monma et al. are the inventors of a better performing formulation, combining $\alpha$-TCP with DCPD as reagents. They found the setting time to be between 9 and 30 minutes.

The product resulting from the setting reaction was OCP which porosity was approximately 50% and the compression resistance was comprised between 14 and 15 MPa.

Concerning the formulation based on HA, this powder product with the addition of between 2 and 4% of CaO and between 2 and 6% ZnO was mixed in a chitosan solution that, as well known, is a peptide derived from chitine in a solution of malic acid.

The setting time, measured by means of an adherence test, varied from 2½ to 20 minutes being the compression resistance in dry state of 2 MPa.

Concerning the formulations using collagen as modifier, $\alpha$-TCP or TTCP in powder form have been combined with an antigenic collagen solution to obtain hardened products, no information having been given on setting time.

The compression resistance in the dry state was approximately 15 MPa and it has been found that when the liquid medium contained citric or malonic acid the compression resistance in dry state increased up to approximately 110 MPa.

Given the fact that the products obtained in these formulations were not calcium phosphates, these materials must not be called calcium phosphate cements and no data have been given concerning its resistance on aging in presence of humidity.

In an experiment by Oonishi and Collaboratorators carried out with test animals, a α-TCP with citric acid was used.

A histological investigation after three years demonstrated that Ca-citrate accumulated in the osteocites and that the α-TCP was transformed into apatite.

Recently a new calcium phosphate bioactive cement has been developed by Nishimura et al. 1991 .

This powder compound is a $CaO$—$SiO_2$—$P_2O_3$—$CaF_2$ system glass.

The powder is blended with an amonic phosphate water solution for 1 minute, with pH 7.4, and a rate liquid/powder of 0.5.

The mix sets in 7½ minutes at 20° C. and its compression resistance is of approximately 16 MPa. However, after its implantation in the hindolimbar muscles of rats said resistance increased up to 70 MPa one week after its implantation.

DISCLOSURE OF THE INVENTION

The process for the preparation of calcium phosphate cements and their use as bio-materials according to the invention, provides by itself a solution to the problems now existing in this field.

Particularly, to carry out this process for the preparation of calcium phosphate cements and their use as bio-materials, a number of pre-requisites have to be taken into account for the use of these calcium orthophosphate cements as bio-materials, which in the first place have to see with its field of application.

As a definition, we will only call calcium orthophosphate cements, formulations in which the setting is provoked or accompanied by the formation of one or more calcium orthophosphate precipitates.

In the setting and surgical handling of this material, the use of calcium orthophosphate cements as bio-materials allows the molding of these basic materials during the surgical intervention.

To prevent the formation of cleavages and fluxes, this molding operation has to be carried out while the cement mix shows visco-elastic properties.

The inventor have used Gilmore needle to determine the end of the visco-elastic period as initial setting time I.

After setting time I there is a certain period in which the cement will not admit any filler, even in small quantities, to avoid the danger of originating cleavages. Even in applications of the type called load-less or devoid of load support, the surgical handling during the intervention will apply some load to the material.

The inventor have used Gilmore heavy needle to determine the time from the beginning of the blend (final setting time F) when the material is sufficiently strong to support the continuation of the intervention.

With the aim to maintain the intervention time within reasonable limits, the inventors have accepted F (or final setting time)=60 minutes as maximum.

Concerning the setting process in relation with the contact with body fluids, in the process for the use of calcium orthophosphate cements as bio-materials, it has to be taken into account that these materials come into contact with the body fluids prior to reaching the initial setting time I.

Therefore, there is still another pre-requisite necessary for the application of calcium orthophosphate cements as bio-materials. Whenever a cement mix contacts a water solution or is submitted to relative humidity of 100% at a physiological temperature before the initial setting time I, and these conditions are maintained for a certain period of time (for example, a minimum of 20 hours) the cement must harden as defined by the test carried out with Gilmore heavy needle.

Certain minimum values for compression resistance and tensile resistance have been found as desirable even for load less applications. These values have been determined in the present state of the art to be approximately 36 MPa for compression resistance and approximately 6 MPa for diametral tensile resistance for calcium orthophosphate cements under ideal physical conditions.

However, according to experience in orthopedics, for load supporting applications a compression resistance of at least 100 MPa under real physiological conditions, even after contacting body fluids or under 100% relative humidity would be necessary.

At present, the use of calcium orthophosphate cements as bio-materials must be limited to applications which do not support loads until in the future a higher resistance may be obtained.

However, it is thought that even for applications without load, a higher compression and tensile strength will be, up to a certain point, desirable characteristics.

These characteristics may be used to rate the quality of calcium orthophosphate cements as bio-materials at least in the applications which do not support loads.

Concerning the minimum resistance to breakage as a necessary pre-requisite for non-supporting load applications for calcium orthophosphate cements as bio-materials, it has been observed from experience in orthopedics that a minimum breakage resistance is necessary for the use of bio-materials in applications which have to support loads.

For the time being, the inventor does not have any evidence that calcium orthophosphate cements are desirable for load supporting applications. However, when reaching a higher development, a minimum breakage resistance will have to be formulated.

Concerning the choice of stability "in vivo" or reabsorption "in vivo" as desirable characteristics for the use of calcium orthophosphate cements as bio-materials, the surgeons consider that for certain applications the calcium phosphate bio-materials should be more reabsorbable for applications "in vivo" and that for other applications they should be reabsorbable.

According to recent investigations, the most reabsorbable calcium orthophosphates are those consisting of mainly of β-TCP, considering that all other calcium phosphates, after a certain period of time, will be in a situation of low reabsorbability.

It is of vital importance for the surgeon to have the possibility of choosing between more or less reabsorbable calcium orthophosphate cements.

To implement this process, first components as they have been described, will have to be comminuted to obtain a grain size of approximately between 5 and 10 um.

Afterwards, the adequate quantities will be weighed, putting the blend of powder product into a bottle or container provided with ample mouthpiece, filling it up to a maximum of 25% of the total volume or capacity of the container.

Subsequently shaking action will be carried out on the container by rotation in the same on a roller for an hour, eventually substituting this action for a vigorous manual shaking for 5 minutes.

Afterwards, the blend which has been obtained will be put in portions in bottles or containers for its supply to surgeons or dentists together with capsules containing the desired quantity of water or water solution.

By last, the bottles and capsules with its contents will be sterilized.

For its use in hospitals or health centers the powder product and the liquid will be supplied together on glass plates or small tiles to obtain a paste after mixing for one minute.

In case of injectable cements, the paste will be put in the added injection and the surgeon or dentist will carry out the injection of the paste into the body.

In case of cements not to be injected, the paste will be applied to the body by means of a palette knife.

BEST MODE TO CARRY OUT THE INVENTION

The process for the preparation of calcium phosphate cements and its use as bio-materials is implemented in a first embodiment with powder blends composed of up to four reagents chosen from the following:

$Ca(H_2PO_4)_2$—$H_2O$, $CaHPO_4$—$2H_2O$, $Ca_8(HPO_4)_2(PO_4)_4$—5 $H_2O$, $\beta$-$Ca_3(PO_4)_2$, $\alpha$-$Ca_3(PO_4)_2$, $Ca_4Mg_5(PO_4)_6CaO$, $Ca(OH)_2$, $CaCo_3$, $CaMgO_2$, $CaHPO_4$, $CaNaPO_4$, $Ca_{10}Na(PO_4)_7$, $Ca_2PO_4Cl$ and $Ca_{10}(PO_4)_6Cl_2$.

The composition of these powder blends was chosen such that the structure formed by the reaction is: DCPD, OCP, CDA, PHA, NCCA or HCDHA.

These powder blends contained crystal seeds of DCPD, SHA or PHA or alternatively, they did not contain any seeds.

This composition choice fulfills the above-stated prerequisites concerning the field of application, that is, by definition, only those formulations which the setting is provoked or is accompanied by the formation of one or more precipitates of calcium orthophosphate will be called calcium orthophosphate cements.

Also, some quantities of these powder blends were mixed with minimum quantities of water giving a consistent paste as result.

Metal rings were filled with this paste and the initial setting time I and the final setting time F at 35° C. were measured with Gilmore needle, with the objective of verifying whether the above-stated requisite was fulfilled concerning the setting and surgical handling of the material.

One of these metal rings for this paste was stored in a relative humidity of 100% at approximately 35° C. for about 20 hours.

Subsequently the resistance was measured by means of Gilmore heavy needle to verify that the requisite setting and contact with body fluids which has been mentioned in the aforegoing, was duly fulfilled.

The blends of powder products appearing in the following table, both those which contained crystal seeds as well as those which did not contain them, fulfilled the requisites concerning the application field, the setting and surgical handling of the material and the setting and contact with body fluids.

In following Table 4 a list of examples will be given for calcium orthophosphate cements setting in 60 minutes or less, which maintain their hardness after being kept at least for 20 hours in 100% relative humidity. In the table:

Column 1 refers to the number of the formulation.

Columns 2 to 5 refer to the reagents.

Column 6 refers to the Ca/P molar relation of the blend of reagents.

Column 7 refers to the type of crystal seeds.

Column 8 refers to the percentage of weight of the seeds in the powder cement.

Column 9 refers to the initial setting time (I) approximately at 37° C.

Column 10 refers to the final setting time (F) approximately at 37° C.

TABLE 4

| 1 | 2 | 3 | 4 | 5 | 6 | 7 | 8 | 9 | 10 |
|---|---|---|---|---|---|---|---|---|---|
| 1 | OCP | Ca(OH)$_2$ | — | — | 1.50 | PHA | 40 | 25 | 55 |
| 2 | MCPM | CaO | — | — | 1.50 | PHA | 40 | 15 | 30 |
| 3 | MCPM | CaO | — | — | 1.67 | PHA | 40 | 8 | 20 |
| 4 | $\alpha$-TCP | — | — | — | 1.50 | PHA | 40 | 20 | 60 |
| 5 | DCP | CaO | CaMgO$_2$ | — | 1.28 | $\beta$-TCP | 40 | 5 | 18 |
| 6 | MCPM | TTCP | — | — | 1.50 | PHA | 40 | 20 | 60 |
| 7 | DCP | TTCP | — | — | 1.50 | PHA | 40 | 15 | 50 |
| 8 | DCP | TTCP | — | — | 1.50 | — | — | 25 | 45 |
| 9 | DCP | TTCP | — | — | 1.67 | — | — | 10 | 25 |
| 10 | DCPD | TTCP | — | — | 1.50 | PHA | 40 | 15 | 50 |
| 11 | DCPD | TTCP | — | — | 1.67 | — | — | 5 | 35 |
| 12 | MCPM | $\beta$-TCP | — | — | 1.00 | DCPD | 10 | 2 | 2 |
| 13 | MCPM | $\beta$-TCP | — | — | 1.00 | — | — | 1 | 2 |
| 14 | MCPM | TTCP | — | — | 1.00 | DCDP | 10 | 5 | 10 |
| 15 | DCPD | $\alpha$-TCP | — | — | 1.33 | PHA | 40 | 15 | 60 |
| 16 | DCPD | TTCP | — | — | 1.33 | PHA | 40 | 15 | 60 |
| 17 | MCPM | $\alpha$-TCP | — | — | 1.33 | PHA | 40 | 10 | 60 |
| 18 | MCPM | TTCP | — | — | 1.33 | PHA | 40 | 25 | 60 |
| 19 | MCPM | CaO | — | — | 1.33 | PHA | 40 | 10 | 30 |
| 20 | DCP | $\alpha$-TCP | — | — | 1.33 | PHA | 40 | 10 | 55 |
| 21 | DCP | TTCP | — | — | 1.33 | PHA | 40 | 15 | 50 |

TABLE 4-continued

| 1 | 2 | 3 | 4 | 5 | 6 | 7 | 8 | 9 | 10 |
|---|---|---|---|---|---|---|---|---|---|
| 22 | DCP | β-TCP | CaMgO$_2$ | — | 1.33 | β-TCP | 40 | 15 | 25 |
| 23 | MCPM | α-TCP | CaMgO$_2$ | — | 1.28 | β-TCP | 40 | 20 | 55 |
| 24 | DCP | α-TCP | CaMgO$_2$ | — | 1.28 | β-TCP | 40 | 15 | 30 |
| 25 | DCP | TTCP | CaMgO$_2$ | — | 1.28 | β-TCP | 40 | 20 | 30 |
| 26 | DCPD | TTCP | CaMgO$_2$ | — | 1.28 | β-TCP | 40 | 20 | 45 |
| 27 | DCP | CaO | CaCO$_3$ | — | 2.00 | PHA | 40 | 6 | 50 |
| 28 | DCPD | CaO | CACO$_3$ | — | 2.00 | PHA | 40 | 5 | 50 |
| 29 | DCP | Ca(OH)$_2$ | CaCO$_3$ | — | 2.00 | PHA | 40 | 10 | 60 |
| 30 | NaWH | CIA | — | — | 1.50 | PHA | 40 | 20 | 55 |
| 31 | Rh | CIA | — | — | 1.50 | PHA | 40 | 10 | 60 |
| 32 | DCP | Rh | CaO | CaCO$_3$ | 1.87 | PHA | 40 | 10 | 45 |
| 33 | CaO | CaKPO$_4$ | Sp | — | 1.67 | PHA | 40 | 13 | 60 |
| 34 | DCPD | CaKPO$_4$ | Sp | — | 1.33 | PHA | 40 | 15 | 35 |
| 35 | NaWH | CIA | DCP | — | 1.33 | PHA | 40 | 15 | 60 |
| 36 | NaWH | CIA | DCP | — | 1.33 | PHA | 40 | 6 | 50 |
| 37 | NaWH | CIA | MCPM | — | 1.00 | DCPD | 40 | 4 | 13 |
| 38 | MCPM | CaO | — | — | 1.50 | SHA | 40 | 5 | 25 |
| 39 | DCP | TTCP | — | — | 1.50 | SHA | 40 | 10 | 40 |
| 40 | OCP | TTCP | — | — | 1.50 | PHA | 40 | 8 | 60 |
| 41 | MCPM | α-TCP | — | — | 1.33 | PHA | 40 | 20 | 50 |
| 42 | MCPM | α-TCP | CaMgO$_2$ | — | 1.28 | — | — | 13 | 25 |
| 43 | DCP | α-TCP | — | — | 1.33 | — | — | 20 | 45 |
| 44 | OCP | Ca(OH)$_2$ | — | — | 1.50 | PHA | 40 | 25 | 55 |
| 45 | MCPM | CaO | — | — | 1.50 | — | — | 8 | 30 |
| 46 | DCP | CaO | — | — | 1.50 | — | — | 15 | 20 |
| 47 | MCPM | CaO | CaMgO$_2$ | — | 1.28 | — | — | 10 | 50 |
| 48 | DCP | CaO | CaMgO$_2$ | — | 1.28 | — | — | 10 | 50 |
| 49 | DCPD | CaO | CaMgO$_2$ | — | 1.28 | — | — | 25 | 45 |
| 50 | MCPM | TTCP | — | — | 1.50 | — | — | 16 | 60 |
| 51 | MCPM | TTCP | — | — | 1.33 | — | — | 5 | 46 |
| 52 | MCPM | CaO | — | — | 1.33 | — | — | 8 | 35 |
| 53 | MCPM | CaO | — | — | 1.33 | SHA | 40 | 8 | 30 |
| 54 | DCP | TTCP | — | — | 1.33 | — | — | 15 | 25 |
| 55 | DCP | CaO | — | — | 1.33 | — | — | 7 | 13 |
| 56 | MCPM | β-TCP | CaMgO$_2$ | — | 1.28 | — | — | 15 | 50 |
| 57 | DCP | β-TCP | CaMgO$_2$ | — | 1.28 | — | — | 20 | 35 |
| 58 | NaWH | CIA | — | — | 1.50 | — | — | 20 | 50 |
| 59 | MCPM | CaO | CaCO$_3$ | — | 2.00 | — | — | 10 | 25 |
| 60 | CaHPO$_4$ | Sp | CaO | — | 1.80 | — | — | 8 | 55 |

In a second embodiment, the cement bodies were prepared according to the powder blends shown in the aforegoing table, in a multiple teflon mould.

Each of the cement bodies has a cylindrical form with a diameter of 6 millimeters and a height of 12 millimeters.

Before setting, the molds were warmed to about 35° C. with a relative humidity of 100%, being maintained in these conditions for at least 20 hours.

The compression resistance was determined (being n comprised between 4 and 8) as well as the diametral tensile resistance (n comprised between 4 and 8).

Table 4 lists the blends with a compression resistance of 1.10 MPa or higher, these elements satisfying, at least to a certain degree, the requisite relative to certain minimum compression and tensile resistance as desirable characteristics, even for applications without load.

It is therefore expected that both the formulations shown in the above table bearing the numbers 5, 22 to 26 and 42 as well as those shown with numerals 47 to 49, 56 and 57 concerning β-TCP and/or MgWH compositions will be more reabsorbable under conditions "in vivo" than the other formulations, for which reason when having this group of cements available, the surgeon may choose calcium orthophosphate cements for use as more or less reabsorbable bio-materials according to the requisite corresponding to the choice of stability "in vivo or reabsorption in vivo" as desirable characteristics for the use of calcium orthophosphate cements as bio-materials, as previously stated.

Table 5 is enclosed which corresponds to calcium orthophosphate cement formulations having a compression resistance of at least 1 MPa after setting and after being stored for at least 20 hours with a relative humidity of 100%. In the table:

Column 1 refers to the formulation number.

Column 2 refers to the rate water/powder in weight.

Column 3 refers to compression resistance (MPa).

Column 4 refers to diametral tensile resistance (MPa).

Column 5 refers to porosity (%).

TABLE 5

| 1 | 2 | 3 | 4 | 5 | 1 | 2 | 3 | 4 | 5 |
|---|---|---|---|---|---|---|---|---|---|
| 1 | 0.6 | 2.9 | 0.5 | — | 38 | 0.50 | 1.5 | 0.37 | — |
| 2 | 0.6 | 2.3 | 0.4 | 62 | 41 | 0.45 | 6.3 | 1.5 | 41 |
| 4 | 0.5 | 2.7 | 0.5 | 62 | 42 | 0.55 | 12.0 | 2.8 | 47 |
| 5 | 0.3 | 1.0 | 0.3 | 43 | 43 | 0.30 | 9.9 | 2.1 | — |
| 7 | 0.5 | 4.8 | 1.1 | 47 | 47 | 0.70 | 2.1 | 0.6 | 55 |
| 8 | 0.3 | 1.0 | 0.06 | 38 | 50 | 0.50 | 4.9 | 1.5 | 42 |
| 12 | 0.5 | 1.7 | 0.7 | 47 | 51 | 0.50 | 2.8 | 0.8 | 47 |
| 14 | 0.4 | 3.6 | 0.4 | 67 | 52 | 0.60 | 1.3 | 0.23 | 55 |
| 15 | 0.55 | 5.6 | 1.2 | 45 | 53 | 0.50 | 3.2 | 0.7 | 49 |
| 16 | 0.55 | 1.6 | 0.4 | 53 | 54 | 0.30 | 2.4 | 0.8 | 42 |
| 17 | 0.65 | 5.2 | 1.0 | 54 | 56 | 0.50 | 1.1 | 0.25 | 51 |
| 18 | 0.70 | 1.0 | 0.23 | 55 | 60 | 0.30 | 1.1 | 0.31 | 38 |
| 20 | 0.50 | 2.3 | 0.55 | 50 | | | | | |
| 21 | 0.55 | 1.2 | 0.27 | 52 | | | | | |
| 23 | 0.55 | 5.9 | 1.8 | 51 | | | | | |
| 30 | 0.35 | 1.2 | 0.27 | 42 | | | | | |

TABLE 5-continued

| 1 | 2 | 3 | 4 | 5 | 1 | 2 | 3 | 4 | 5 |
|---|---|---|---|---|---|---|---|---|---|
| 34 | 0.35 | 2.1 | — | — | | | | | |
| 35 | 0.50 | 1.0 | 0.16 | 48 | | | | | |
| 36 | 0.50 | 1.3 | 0.28 | 50 | | | | | |

The process which is necessary to obtain the calcium phosphate cements of the invention is carried out as explained in this description, starting with the components which have been described in the aforegoing, which have to be ground and passed through a sieve up to the desired grain size which is approximately between 5 and 10 microns.

Subsequently, they will be weighed according to the adequate quantity, after which the blend of powder products will be used to fill a bottle or wide mouth container, filling it up to a maximum of 25% of its capacity.

The bottle or container will be submitted to rotation on a roller for one hour or alternatively it will be shaken vigorously by hand for 5 minutes.

The mix will be placed afterwards, in the desired portions, in bottles for its supply to surgeons or dentists together with capsules which contain the desired quantity of water or water solution.

Finally, the bottles as well as the capsules with their contents will be sterilized.

For use in a hospital or health center the powder product and the liquid will be supplied together with a glass plate or tile, to be mixed for one minute until a paste is obtained.

In case of injectable cements said paste will be placed in the added injection and the surgeon or dentist will proceed to the injection into the body.

In case of non-injectable cements the paste will be applied on the body, specifically to bone tissue, by means of a palette knife. The paste is then exposed to moisture at body temperature, thereby causing said cement to cure.

A more detailed explanation of the invention is not deemed necessary for the understanding of the same by those of skill in the art in order to carry out the invention and to recognize its advantages.

The material as well as its shape, size and disposition of the components or products will be variable wherever this does not mean a change in the essentials on the invention.

I claim:

1. A calcium orthophosphate paste consisting essentially of a water mix, with a pH of 6.5 to 8, of three or four calcium compounds selected from the group consisting of $Ca(H_2PO_4)_2$—$H_2O$, $CaHPO_4$, $CaHPO_4$—$2H_2O$, $Ca_8(HPO_4)_2(PO_4)_4$—5 $H_2O$, $\beta$-$Ca_3(PO_4)_2$, $\alpha$-$Ca_3(PO_4)_2$, $Ca_{10}(PO_4)_6(OH)_2$, $Ca_{8.5}Na_{1.5}(PO_4)_{4.5}(CO_3)_{2.5}$, $Ca_9(PO_4)_{4.5}(CO_3)_{1.5}$, $Ca_4Mg_5(PO_4)_6$, $CaZn_2(PO_4)_2$, $CaKPO_4$, $CaNaPO_4$, $Ca_{10}Na(PO_4)_7$, $Ca_2PO_4Cl$, $CaO$, $Ca(OH)_2 CaMgO_2$ and $Ca_{10}(PO_4)_6Cl_2$, wherein at least one of said calcium compounds is a calcium phosphate said paste having the capacity to harden to a bio-compatible calcium phosphate cement when subjected to 100% relative humidity.

2. A calcium phosphate paste according to claim 1 wherein the calcium orthophosphate paste further consists essentially of one or more compounds selected from the group consisting of $MgO$, $MgCO_3$, $Mg(OH)_2$, $ZnO$, $ZnCO_3$, and Na, K, Mg or Zn orthophosphates.

3. A calcium phosphate paste according to claims 1 or 2, wherein the calcium orthophosphate paste further consists essentially of one or more compounds selected from the group consisting of chlorides, carbonates or sulfates of sodium, potassium, magnesium, zinc, or calcium, proteins, peptides, proteoglycans, glucoseaminoglycans, carbohydrates, polylactic acid, polyglycolic acid and $\beta$-TGF, where said compounds are used as accelerators, retarders or modifiers.

4. A process for the preparation of calcium phosphate cement consisting essentially of a calcium orthophosphate paste which consists essentially of a water mix, with a pH of 6.5 to 8, of three or four calcium compounds selected from the group consisting of $Ca(H_2PO_4)_2$—$H_2O$, $CaHPO_4$, $CaHPO_4$—$2H_2O$, $Ca_8(HPO_4)_2(PO_4)_4$—5 $H_2O$, $\beta$-$Ca_3(PO_4)_2$, $\alpha$-$Ca_3(PO_4)_2$, $Ca_{10}(PO_4)_6(OH)_2$, $Ca_{8.5}Na_{1.5}(PO_4)_{4.5}(CO_3)_{2.5}$, $Ca_9(PO_4)_{4.5}(CO_3)_{1.5}(OH)_{1.5}$, $Ca_4$, $Mg_5(PO_4)_6$, $CaZn_2(PO_4)_2$, $CaKPO_4$, $CaNaPO_4$, $Ca_{10}Na(PO_4)_7$, $Ca_2PO_4Cl$, $CaO$, $Ca(OH)_2$, $CaMgO_2$ and $Ca_{10}(PO_4)_6Cl_2$, wherein at least one of said calcium compounds is a calcium phosphate comprising the steps of grinding each calcium compound to a powder with a grain or cluster size of about 5 to 10 microns, mixing the ground powdered calcium compounds to form a blend of powder products, and adding water or a water-based solution to form a paste, and curing said paste to form a calcium phosphate cement.

5. A method for using calcium orthophosphate cement said cement comprising a calcium orthophosphate paste which consists essentially of a water mix, with a pH of 6.5 to 8, of three or four calcium compounds selected from the group consisting of $Ca(H_2PO_4)_2$—$H_2O$, $CaHPO_4$, $CaHPO_4$—$2H_2O$, $Ca_8(HPO_4)_2(PO_4)_4$—5 $H_2O$, $\beta$-$Ca_3(PO_4)_2$, $\alpha$-$Ca_3(PO_4)_2$, $Ca_{10}(PO_4)_6(OH)_2$, $Ca_{8.5}Na_{1.5}(PO_4)_{4.5}(CO_3)_{1.5}$, $Ca_9(PO_4)_{4.5}(CO_3)_{1.5}(OH)_{1.5}$, $Ca_4Mg_5(PO_4)_6$, $CaZn_2(PO_4)_2$, $CaKPO_4$, $CaNaPO_4$, $Ca_{10}Na(PO_4)_7$, $Ca_2PO_4Cl$, $CaO$, $Ca(OH)_2$, $CaMgO_2$ and $Ca_{10}(PO_4)_6Cl_2$, wherein at least one of said calcium compounds is a calcium phosphate comprising the steps of:

preparing said calcium orthophosphate paste by grinding each calcium compound to a powder with a grain or cluster size of about 5 to 10 microns, mixing the ground, powdered calcium compounds, and adding water or a water-based solution;

applying said paste to bone tissue;

exposing said paste to moisture at body temperature thereby causing said paste to cure to a calcium orthophosphate cement.

6. A method according to claim 5 where said calcium orthophosphate paste further consists essentially of one or more compounds selected from the group consisting of MgO, $MgCO_3$, $Mg(OH)_2$, ZnO, and Na, K, Mg or Zn orthophosphates.

7. A method according to claim 6 where said calcium orthophosphate paste further consists essentially of one or more compounds selected from the group consisting of chlorides, carbonates or sulfates of sodium, potassium, magnesium, zinc, or calcium, proteins, peptides, proteoglycans, glucoseaminoglycans, carbohydrates, polylactic acid, polyglycolic acid and β-TGF, where said additional compounds are used as accelerators, retarders or modifiers.

8. A method according to claim 5 where said calcium orthophosphate paste further consists essentially of one or more compounds selected from the group consisting of $CaHPO_4$—$2H_2O$, $Ca_8(HPO_4)_2(PO_4)_4$—$5H_2O$, precipitated hydroxyapatite, sintered hydroxyapatite, sodium—and carbonate containing apatite, $Ca_8(PO_4)_{4.5}(CO_3)_{1.5}(OH)_{1.5}$ and minerals extracted from calcified tissues, where said compounds are used as crystal seeds.

9. A method according to claim 5 where said calcium orthophosphate paste further consists essentially of water solutions at least one soluble compound selected from the group consisting of chlorides, carbonates, or sulfates of sodium, potassium, magnesium, zinc, or calcium, proteins, peptides, proteoglycans, glucoseaminoglycans, carbohydrates, polylactic acid, polyglycolic acid and β-TGF.

* * * * *

UNITED STATES PATENT AND TRADEMARK OFFICE
CERTIFICATE OF CORRECTION

PATENT NO. : 5,605,713

DATED : February 25, 1997

INVENTOR(S): MARIA G. BOLTONG

It is certified that error appears in the above-identified patent and that said Letters Patent is hereby corrected as shown below:

On the title page, item
[76] INVENTOR

"Menzenlaan 12," should read --Mezenlaan, 12--.

[56] REFERENCES CITED

Other Publications
Under "F.C.M Driessens and R.M.H. Verbeeck":
"tion Elsevier," should read --tion, Elsevier,--
and "H. Oonish; Orthopaedic applications of
Hydroxyapatite, Biomaterials v. 12 171-178 (1991)
no month." should be deleted.

COLUMN 1

Line 14, "which obvious objective is" should read
--with the obvious objective --.

COLUMN 2

Line 29, "consequence," should read --a consequence,--.
Line 38, "table 1:" should read --Table 1:--.
Table 1, Under "Formation conditions": "whitlockite NWH"
should read --whitlockite. MWH-- and "maybe" should
read --may be--.

COLUMN 3

Line 23, "specially" should read --especially--.

UNITED STATES PATENT AND TRADEMARK OFFICE
CERTIFICATE OF CORRECTION

PATENT NO. : 5,605,713

DATED : February 25, 1997

INVENTOR(S) : MARIA G. BOLTONG

It is certified that error appears in the above-identified patent and that said Letters Patent is hereby corrected as shown below:

COLUMN 4

Table 3, Under "Potassium": "*CAKPO$_4$," should read
--*CaKPO$_4$,--.

COLUMN 5

Table 3, "glucoseamoglycans," should read
--glucoseaminoglycans,--.
Line 59, "with," should read --with DCPP,--.

COLUMN 6

Line 16, "between" should read --between 6--.
Line 17, "50% (4)." should read --50%.--.
Line 27, "by." should read --by-- and close up right margin.
Line 28, "By" should be deleted and close up left margin.

COLUMN 7

Line 11, "Collaboratorators" should read --collaborators--.
Line 12, "a" should read --an--.
Line 20, "amonic" should read --ammonia--.
Line 21, "rate" should read --ratio--.
Line 36, "pre-requisites" should read --prerequisites--.
Line 38, "see" should read --do--.

UNITED STATES PATENT AND TRADEMARK OFFICE
CERTIFICATE OF CORRECTION

PATENT NO. : 5,605,713

DATED : February 25, 1997

INVENTOR(S) : MARIA G. BOLTONG

It is certified that error appears in the above-identified patent and that said Letters Patent is hereby corrected as shown below:

COLUMN 7 (Cont.)

Line 52, "have" should read --has--.
    Line 61, "have" should read --has--.
    Line 66, "inventors have" should read --inventor has--.

COLUMN 8

Line 6, "pre-requisite" should read --prerequisite--.
    Line 16, "load" should read --load---.
    Line 39, "pre-requisite" should read --prerequisite--.

COLUMN 9

Line 13, "By last, the" should read --The--.
    Line 29, "its" should read --their--.
    Line 34, "$(PO_4)_6CaO$," should read --$(PO_4)_6$, CaO,--.

COLUMN 11

Table 4, "CACO$_3$" should read --CaCO$_3$-- and under
      Column 10: "46" should read --45--.
    Line 51, "elements" should read --cements--.

UNITED STATES PATENT AND TRADEMARK OFFICE
CERTIFICATE OF CORRECTION

PATENT NO. : 5,605,713

DATED : February 25, 1997

INVENTOR(S): MARIA G. BOLTONG

It is certified that error appears in the above-identified patent and that said Letters Patent is hereby corrected as shown below:

COLUMN 12

Line 38, "is enclosed which" should be deleted.
Line 45, "rate" should read --ratio--.
Line 59, "67" should read --57--.

COLUMN 13

Line 59, "Ca(OH)$_2$CaMgO$_2$" should read --Ca(OH)$_2$, CaMgO$_2$--.
Line 60, "phosphate" should read --phosphate,--.

COLUMN 14

Line 21, "Ca$_4$, Mg$_5$(PO$_4$)$_6$," should read --Ca$_4$Mg$_5$(PO$_4$)$_6$,--.
Line 32, "cement" should read --cement,--.
Line 44, "phosphate" should read --phosphate,--.

COLUMN 15

Line 7, "sodium——and" should read --sodium- and--.
Line 8, "bonate containing" should read --bonate-containing--.

UNITED STATES PATENT AND TRADEMARK OFFICE
CERTIFICATE OF CORRECTION

PATENT NO. : 5,605,713

DATED : February 25, 1997

INVENTOR(S) : MARIA G. BOLTONG

It is certified that error appears in the above-identified patent and that said Letters Patent is hereby corrected as shown below:

<u>COLUMN 16</u>

Line 3, "solutions" should read --solutions of--.

Signed and Sealed this

Sixth Day of January, 1998

Attest:

BRUCE LEHMAN

Attesting Officer

Commissioner of Patents and Trademarks